(12) United States Patent
DeFreitas et al.

(10) Patent No.: US 8,948,340 B2
(45) Date of Patent: *Feb. 3, 2015

(54) MAMMOGRAPHY SYSTEM AND METHOD EMPLOYING OFFSET COMPRESSION PADDLES, AUTOMATIC COLLIMATION, AND RETRACTABLE ANTI-SCATTER GRID

(71) Applicant: Hologic, Inc., Bedford, MA (US)

(72) Inventors: Kenneth DeFreitas, Patterson, NY (US); Anthony Pellegrino, New Fairfield, CT (US); Thomas A Farbizio, Newtown, CT (US); Roman Janer, Commerce Township, MI (US); Georgia Hitzke, Boston, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/052,825

(22) Filed: Oct. 14, 2013

(65) Prior Publication Data

US 2014/0098935 A1    Apr. 10, 2014

Related U.S. Application Data

(63) Continuation of application No. 13/190,989, filed on Jul. 26, 2011, now Pat. No. 8,559,595, which is a continuation of application No. 12/710,184, filed on Feb. 22, 2010, now Pat. No. 7,986,765, which is a (Continued)

(51) Int. Cl.
*A61B 6/04*  (2006.01)
*A61B 6/00*  (2006.01)
*A61B 6/06*  (2006.01)

(52) U.S. Cl.
CPC ............... *A61B 6/04* (2013.01); *A61B 6/0414* (2013.01); *A61B 6/4233* (2013.01); *A61B 6/502* (2013.01); *A61B 6/4291* (2013.01); *A61B 6/06* (2013.01)
USPC ............................................................ 378/37

(58) Field of Classification Search
CPC ........ A61B 6/0414; A61B 6/06; A61B 6/502; A61B 6/4233; A61B 6/4291
USPC ........................................ 378/37, 20, 68, 208
See application file for complete search history.

(56) References Cited

U.S. PATENT DOCUMENTS

| 3,502,878 A | 3/1970 | Stewart |
| 3,863,073 A | 1/1975 | Wagner |

(Continued)

OTHER PUBLICATIONS

International Search Report, PCT Application, PCT/US02/33058, mailed Apr. 3, 2003.

(Continued)

*Primary Examiner* — Irakli Kiknadze

(57) ABSTRACT

A mammographic imaging system is optimized for use with a single fixed size flat panel digital image receptor. It accommodates compression devices (paddles) of varying sizes, and positions them properly in a field of view of the image receptor. When a compression paddle with size smaller than the field of view of the image receptor is used, the compression paddle can be shifted laterally in the direction parallel to the chest wall, so as to facilitate different views of different size breasts, and permit the image receptor to image as much of the desired tissue as possible. An automatic X-ray collimator restricts the X-ray illumination of the breast in accordance with the compression paddle size and location in the field of view. An anti-scatter grid, mounted inside the image receptor enclosure, just below the top cover of the enclosure, can be retracted out of the field of view of the image receptor for use in magnification imaging.

19 Claims, 5 Drawing Sheets

Related U.S. Application Data continuation of application No. 12/463,256, filed on May 8, 2009, now Pat. No. 7,688,940, which is a continuation of application No. 12/014,405, filed on Jan. 15, 2008, now Pat. No. 7,609,806, which is a continuation of application No. 11/607,748, filed on Nov. 30, 2006, now Pat. No. 7,319,735, which is a continuation of application No. 10/496,049, filed as application No. PCT/US02/33058 on Oct. 17, 2002, now Pat. No. 7,443,949.

(60) Provisional application No. 60/350,213, filed on Oct. 19, 2001.

(56) References Cited

U.S. PATENT DOCUMENTS

| | | |
|---|---|---|
| 3,971,950 A | 7/1976 | Evans |
| 4,559,641 A | 12/1985 | Caugant |
| 4,663,774 A | 5/1987 | Saffer |
| 4,821,727 A | 4/1989 | Levene |
| 4,947,417 A * | 8/1990 | Hartwell ................ 378/147 |
| 4,969,174 A | 11/1990 | Scheid |
| 4,989,227 A | 1/1991 | Tirelli |
| RE33,634 E | 7/1991 | Yanaki |
| 5,164,946 A | 11/1992 | Negus |
| 5,164,976 A | 11/1992 | Scheid |
| 5,199,056 A | 3/1993 | Darrah |
| 5,224,147 A * | 6/1993 | Collin et al. .................. 378/162 |
| 5,506,877 A | 4/1996 | Niklason |
| 5,553,111 A | 9/1996 | Moore |
| 5,627,869 A | 5/1997 | Andrew |
| 6,075,879 A | 6/2000 | Roehrig |
| 6,102,866 A * | 8/2000 | Nields et al. .................. 600/461 |
| 6,149,301 A | 11/2000 | Kautzer |
| 6,327,336 B1 | 12/2001 | Gingold |
| 6,625,253 B1 | 9/2003 | Barnes |
| 7,200,199 B2 | 4/2007 | Andreasson |
| 7,315,640 B1 | 1/2008 | Brady |
| 7,319,735 B2 | 1/2008 | DeFreitas |
| 7,443,949 B2 * | 10/2008 | Defreitas et al. ................ 378/37 |
| 7,609,806 B2 | 10/2009 | DeFreitas |
| 7,688,940 B2 | 3/2010 | DeFreitas |
| 7,986,765 B2 | 7/2011 | DeFreitas |
| 2001/0038681 A1 | 11/2001 | Stanton |
| 2002/0012450 A1 | 1/2002 | Tsujii |

OTHER PUBLICATIONS

Senographe 700 & 800T (GE); 2 page download on Jun. 22, 2006 from www.gehealthcare.com/inen/rad/whc/products/mswh800t.html.

* cited by examiner

MAMMOGRAPHY SYSTEM AND METHOD EMPLOYING OFFSET COMPRESSION PADDLES, AUTOMATIC COLLIMATION, AND RETRACTABLE ANTI-SCATTER GRID

RELATED APPLICATIONS

This application is a continuation application and claims priority under 35 U.S.C. §120 to U.S. patent application Ser. No. 13/190,989, filed Jul. 26, 2011, which is a continuation of U.S. Pat. No. 7,986,765, filed on Feb. 22, 2010, which is a continuation of U.S. Pat. No. 7,688,940, filed on May 8, 2009, which is a continuation of U.S. Pat. No. 7,609,806, filed Jan. 15, 2008, which is a continuation of U.S. Pat. No. 7,319,735, filed Nov. 30, 2006, which is a continuation of U.S. Pat. No. 7,443,949, filed Oct. 18, 2004, which is a Section 371 national stage of International Application No. PCT/US02/33058, filed Oct. 17, 2002, claiming the benefit of U.S. Provisional application No. 60/350,213, filed Oct. 19, 2001. Each of the above applications is hereby incorporated by reference.

BACKGROUND

X-Ray mammography machines typically use an x-ray source mounted at one end of a rotatable c-arm assembly and an image receptor at the other. Between the x-ray source and the image receptor is a device for compressing and immobilizing a breast. Until recently, the image receptor was typically a screen-film (s/f) cassette, which generated an image related to the detected transmission of x-rays through the breast. These s/f cassettes typically come in standard sizes, e.g., 18 cm×24 cm (small) and 24 cm×30 cm (large), with the large cassette used when the breast is too large to be uniformly compressed by the small cassette. The cassettes are easily attachable and removable from a breast support tray of a conventional mammography system. The device for compressing the breast is often called a paddle, and comes in a variety of sizes to match both the cassette size and the breast size. Such matching is desirable because the use of a small size paddle on a large breast can result in uneven and inadequate breast compression and may not allow full-breast imaging, which using a large paddle on a small breast can impede access to the breast, which is important during the compression cycle in order to optimize the amount of breast tissue brought into the field of view of the image receptor.

New mammography systems are now being developed to use digital image receptors as replacements for the screen-film cassettes. These digital image receptors, sometimes called flat panel receptors, or flat panel digital x-ray receptors, are different in many ways from s/f cassettes. They have many advantages, but also tend to be heavier and somewhat thicker. Typically, they are not designed to be removable in normal use, so a system normally will employ only one size image receptor. These characteristics can presents challenges for some imaging procedures and breast sizes, particularly for the mediolateral oblique view (MLO) taken as a part of typical breast x-ray imaging. As with screen-film systems, it is still advantageous to use a compression paddle that matches the breast size. This typically means that the compression paddles will be removable, and there will be a selection of paddle sizes available with the system.

A number of x-ray protocols have been used for breast imaging. One common view is the cranio-caudal (CC) view, illustrates in FIG. 5, which images the breast of a standing or sitting patient from above. Another is the mediolateral oblique view (MLO), taken from an oblique or angled view, and also illustrated in FIG. 5. In screen-film mammography systems, the compression paddle typically is centered relative to the proximal edge of the screen-film cassette. In some views, such as the MLO view, and particularly for smaller breasts, this may present some difficulty as the cassette may have to be pressed against the armpit in order to approximately center the breast relative to the proximal edge of the film (the edge closest to and parallel to the chest wall). In such cases, the smaller size cassette can be used. This, plus the relative thinness of the cassette, generally allow for adequate centering. However, when a digital x-ray receptor is used usually only one size is available, and it may be the size comparable to the larger size screen-film cassette. Also, the digital receptor tends to be thicker than a screen-film cassette. Thus, centering the breast can be difficult or impossible in some cases, particularly for the MLO view and patients with smaller breasts, with the result that optimal positioning of the breast may not be possible for some views and patients.

To applicants' knowledge, these and other issues regarding compression paddle use with flat panel digital receptors in mammography have not been solved and perhaps have not been even addressed. In a different setting, it has been proposed to move a compression paddle laterally, relative to the proximal edge of the screen-film cassette, but for the different purposes of aligning a cutout in the paddle with a particular portion of the breast. See U.S. Pat. No. 5,199,056. This is believed to require a paddle larger that would normally be used for the breast size so as to maintain even compression when the cutout is off-center relative to the breast. Other earlier proposals are known for features such as collimation that adjusts to film cassette size, source-to-image distance and/or cross-sectional area to be imaged (U.S. Pat. Nos. 3,502,878, 3,863,073, 5,627,869, and 6,149,301), moving a paddle (U.S. Pat. No. 3,971,950), moving a cassette (U.S. Pat. No. 4,989,227), and retracting a cassette holder (U.S. Pat. No. 4,559,641). The cited patents are hereby incorporated by reference in this patent specification.

SUMMARY

An object of the disclosed system and method is to provide mammography that overcomes known disadvantages of proposals involving the otherwise desirable use of flat panel, digital x-ray receptors.

Another object is to employ compression paddles that match both the size and position of the patient's breast relative to the proximal edge of a digital x-ray image receptor so as to improve image quality, patient comfort and the ability of the health professional to position the breast optimally for imaging.

Another is to provide automated collimation control that changes x-ray beam collimation in accordance with one or more of the size and position of the compression paddle and of the breast, and the position of a breast platform relative to the receptor, preferably in response to information that is automatically sensed.

Another is to provide x-ray exposure control that is responsive to at least one of the size and position of the compression paddle, the position of the breast, and a pre-exposure x-ray measurement, preferably in response to information that is automatically sensed.

Another is to provide a scatter-suppression grid that is retracted for image magnification protocols, preferably automatically in response to sensing a breast position for magnification imaging.

These and other objects are met in a non-limiting example comprising a mammography system having a flat panel digital x-ray receptor, an x-ray source selectively emitting a collimated x-ray beam toward the receptor, and a compression paddle of a selectable size mounted for selective movement at least along a proximal edge of the x-ray receptor as well as along the x-ray beam. At least for selected breast x-ray protocols, a patient's breast is positioned off-center relative to the proximal edge of the x-ray receptor, and paddle of an appropriate size also is positioned off-center relative the same proximal edge to compress the breast for x-ray imaging.

In addition, the system includes one or more of a number of other features. An exposure control can be responsive to information regarding breast thickness along the beam direction to control x-ray exposure for imaging. This information can come from a conventional auto-exposure sensor (AES) resulting from a pre-exposure, low-dose firing of the x-ray source from an output of the digital x-ray receptor during such pre-exposure firing, and/or from sensors for the relative positions of the x-ray source, the x-ray receptor, the compression paddle and/or the breast tray. The system can include a collimation control responsive to information regarding one or more of the size of the paddle, its location along the beam, its location relative to the proximal edge of the receptor, a desired field of view, magnification parameters, and the like. This information can come from appropriate sensors and/or can be input by the health professional carrying out imaging. The system can include a scatter-suppressing grid selectively movable between a position in the path of the imaging beam and a position outside that path (for magnification imaging). Again, information for controlling grid position can come from one or more different sources. And, the system can include a built-in or a separate viewing station receiving x-ray image information from the x-ray receptor and possibly from some or all of the sensors, processing it, and displaying the results as an image and/or in others forms.

DETAILED DESCRIPTION OF THE PREFERRED EMBODIMENTS

Figure 1:
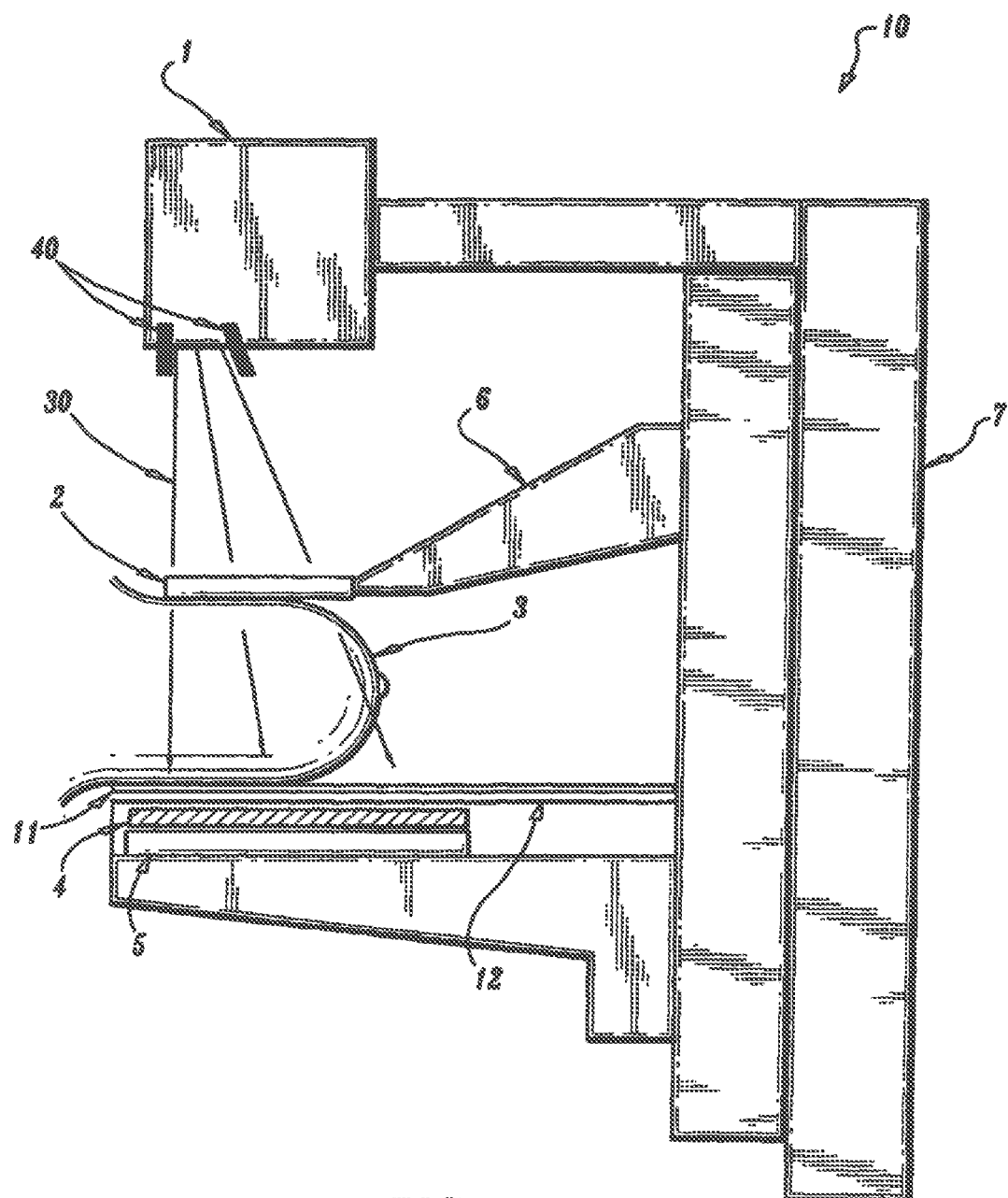
FIG. 1 illustrates a partial side view of a mammography system imaging a patient's breast.

Referring to FIG. 1, an x-ray source 1 is at one end of a generally C-shaped frame 7 and a flat panel digital x-ray imaging receptor 5 is at the other end. X-ray source 1 includes a collimator schematically illustrated at 40 to confine an x-ray beam 30 emitted from source 1 to a desired footprint at receptor 5, typically no larger than the area of receptor 5 and preferably just enough to image a patient's breast 3 or at least a selected part thereof, as compressed toward receptor 5 by a compression paddle 2 mounted on an arm 5 that in turn mounts to frame 7. A lower platform 11, often called a breast tray, is immediately below the breast, and a scatter-reducing grid 4 is between breast tray 11 and x-ray receptor 5 and is housed in the same enclosure 12 with the receptor. As is known in the art, frame 7 can rotate between horizontal and vertical directions of x-ray beam 30.

Figure 2:
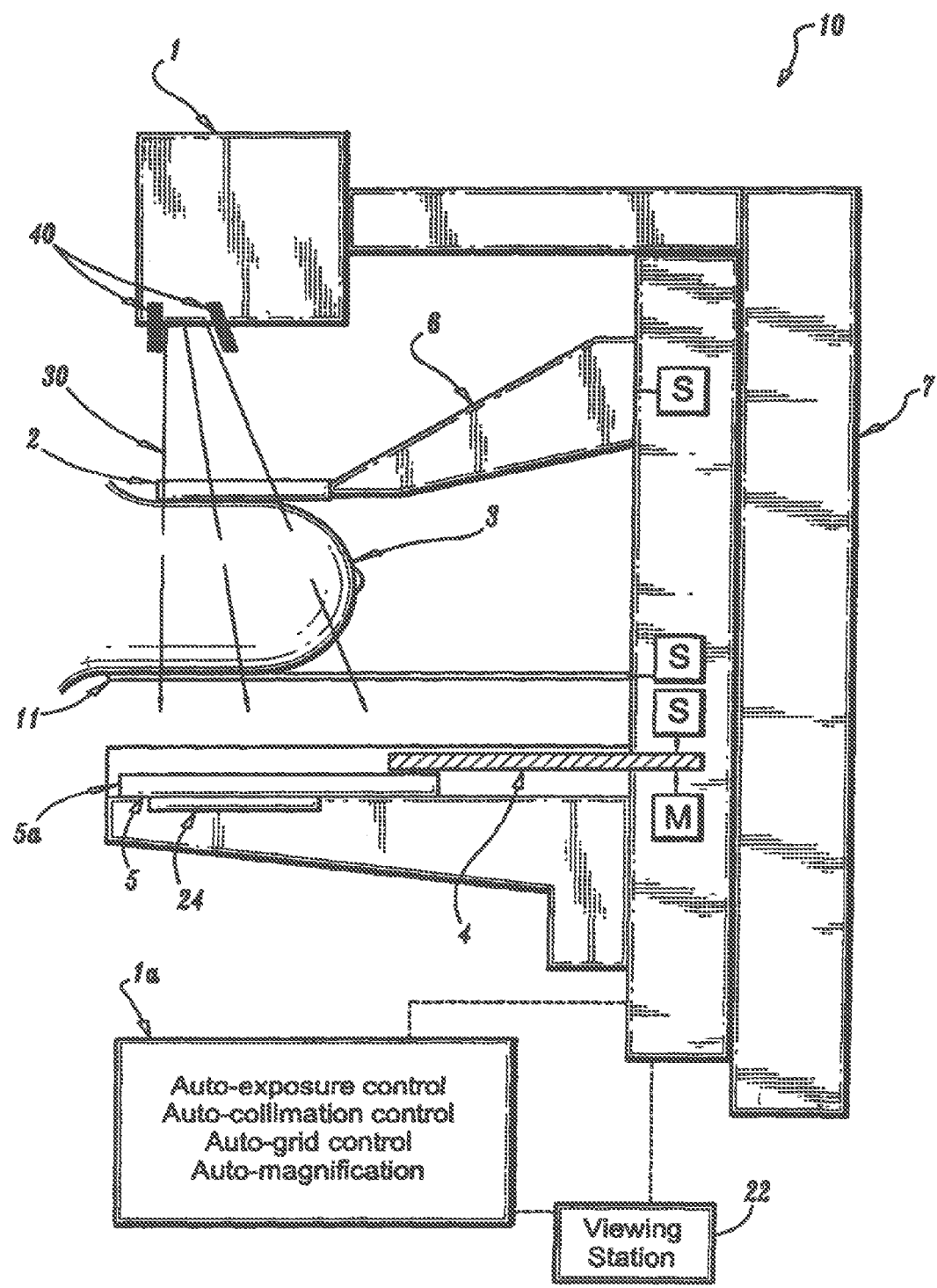
FIG. 2 illustrates the system also in side view but in more detail and in a magnification mode.

In use for a CC view, paddle 2 and its supporting arm 6 are moved up, breast 3 is positioned on tray 11 and compressed by bringing paddle 2 down as needed. With suitable collimation by collimators 40 (which typically collimate in two directions, of which only one is illustrated in FIG. 1), beam 30 from source 1 images the breast onto receptor 5 and the resulting electronic image information is transmitted to a viewing station 22 (FIG. 2). The image typically is rectangular. Preferably, the collimation is such that beam 30 illuminates an area of receptor 5 just large enough to show the image of breast 3, or at least a selected part thereof. Importantly, different sizes and shapes of paddles 2 can be mounted to arm 6, and the paddle can be selectively positioned off-center relative to proximal edge 5a of receptor 5 (the left edge in FIG. 1).

Referring to FIG. 2, the system can operate in a magnification mode in which the relative positions along x-ray beam 30 of source 1, breast try 11, and/or receptor 5 are adjusted to provide the desired image magnification. In this example, source 1 and receptor 5 stay in place but tray 11 slides up support 7 to a position spaced up from receptor 5, and the collimation of beam 30 is adjusted as needed. Note that for magnification imaging scatter-reducing grid 4 is withdrawn from the position of receptor 5 that receives the desired breast image, because the angles of the grid septa typically are not suitable for a magnification view. If these angles can be changed to match the selected magnification, the grid can remain in place. Alternatively and if desired, a different grid that is suitable for the selected magnified view can be introduced in place of grid 4 in FIG. 1. Auto-controls 1a can include (a) an auto-exposure control coupled with an AEC sensor 24 and/or receptor 5 to receive exposure information in a pre-imaging firing of source 1, (b) an auto-collimation control to adjust the collimation of beam 30, (c) an auto-grid control to selectively withdraw grid 4, and (d) an auto-magnification control to adjust parameters for magnification imaging. AEC sensor 24 can be conventional separate sensor that helps determine imaging exposure parameters in a pre-imaging exposure of the immobilized breast at a low x-ray dosage. Alternatively, receptor 5 can be used for that purpose, eliminating the need for a separate AEC sensor, because the output of receptor 5 resulting from a low-dose pre-imaging exposure can provide the information for auto-exposure control. In addition, the output of receptor 5 in response to the pre-imaging exposure can reveal the position of the breast relative to the receptor, and thus provide information for auto-collimation to confine beam 30 to a footprint that matches the breast even when the breast is off-center relative to proximal edge 5a. The auto-collimation control can be an arrangement sensing size and/or the position of one or more of breast 3, paddle 2, and tray 11, using respective sensors and automatically adjusting collimators 40 to confine beam 30 to the required cross-section and position. The auto-grid control can respond to a signal indicating that that magnification imaging will be carried out to withdraw grid 4, for example to the position shown in FIG. 2, using a motor 4a. This signal can come from information provided by respective sensors or it can be input by the health professional using the system. The auto-magnification control can be an arrangement responding the data entered by a health professional through viewing station 22, or in some other way, e.g., based on information from sensors to adjust the system elements involved in magnification. Information for the auto-controls can be provided in various ways. One is from sensors S that keep track of the size and the position of paddle 2 along beam 30 and relative to proximal edge 5a of x-ray receptor 5, of the position of breast tray 11 along beam 30, of the position of grid 4, and the setting of collimators 40. Another is inputs from an auto-exposure sensor and/or x-ray receptor 5 resulting from a pre-exposure firing of beam 30 at low dose, with breast 3 in place for imaging. As is known in the art, the output of receptor 5 can be used to detect the position of breast 3 relative to receptor 5, or at least the approximate position of the breast relative to proximal edge 5a. Yet another possible source of information for the auto-controls is inputs from the health professional using the system, through a keyboard or other input devices in viewing station 22 or elsewhere. Information is exchanged between auto-controls 1a, sensors S, and viewing station 22 over appropriate links, shown schematically. Suitable arrangements, including encoders, motors (of which only motor M retracting and restoring grid 4 is expressly illustrated), and other control elements are included in mammography system 10 but, for clarity of the drawings, are not expressly illustrated.

Figure 3:
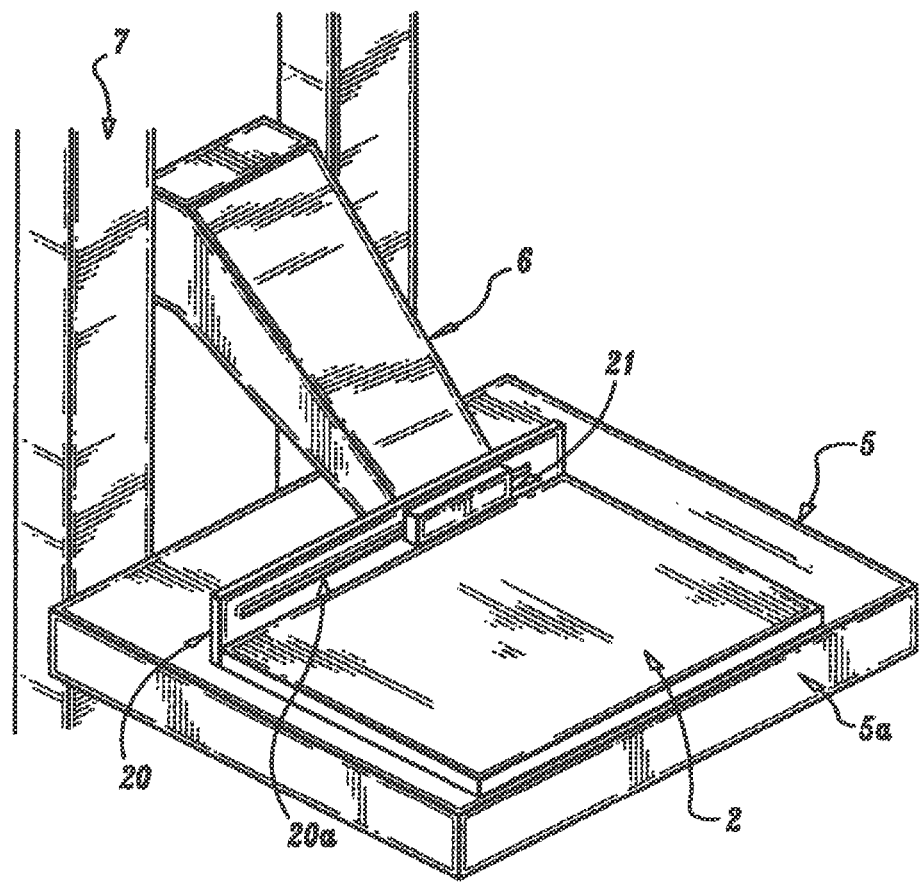
FIG. 3 illustrates a lateral displacement of a small compression paddle along the proximate edge of the image receptor.

FIG. 3 illustrates an example of an arrangement for positioning paddle 2 off-center relative to proximal edge 5a of receptor 5. While such off-center positioning can be used for other views as well, it is most important for views such as the MLO view. As seen in FIG. 3, paddle 2 includes a rib 20 that has a channel slot 20a and is secured to arm 6 with a removable and adjustable lock or detent 21 that passes through channel 20a. In operation, the health professional selects a paddle 2 that is suitable in size and perhaps in shape to the breast to be imaged, removes any existing paddle 2 from arm 6 by pulling out or unscrewing detent 21, and installs the selected paddle 2 by securing it to arm 6 with detent 21 in a position relative to proximal edge 5a that matches the patient's breast's position. Any desired further lateral adjustment can be made by sliding paddle 2 along the direction of the proximal edge 5a, before or during compressing the breast for taking an image.

Figure 4A:
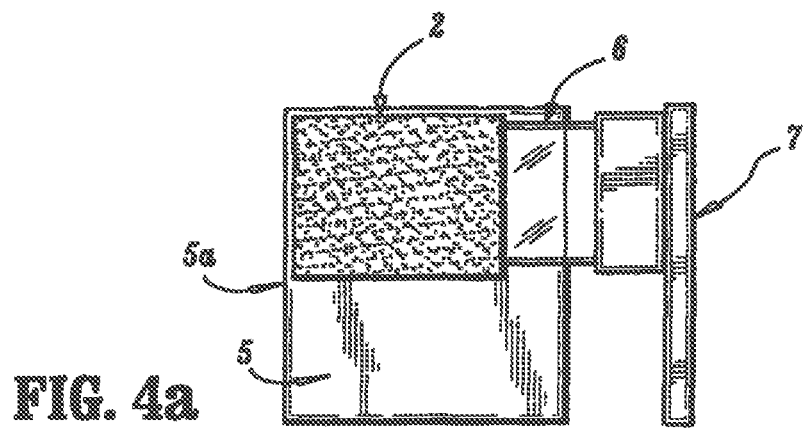
FIGS. 4a-4c show three common positions of a small compression paddle relative to the image receptor.
Figure 4B:
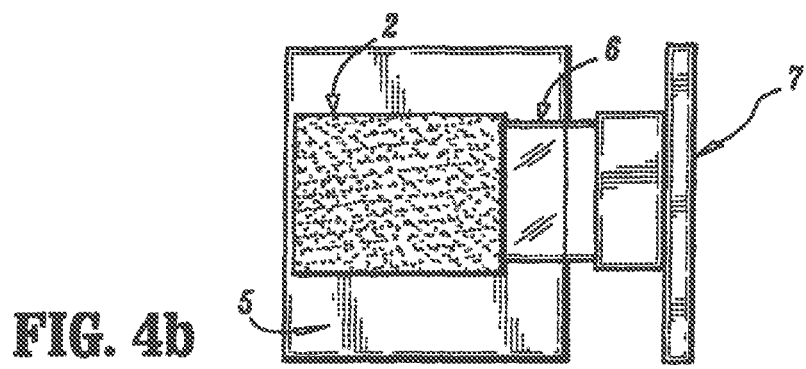
Figure 4C:
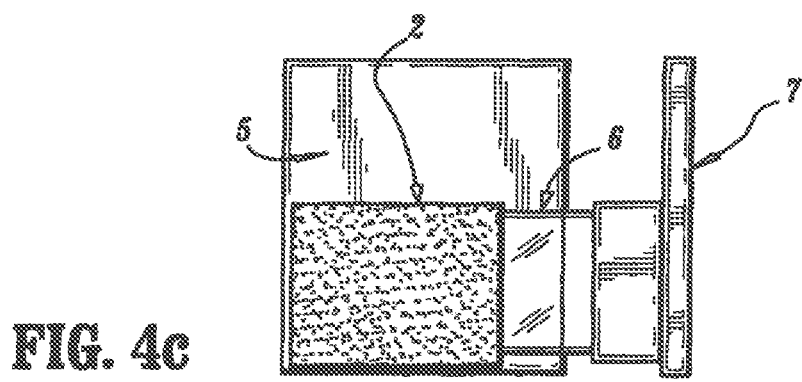
Figure 5:
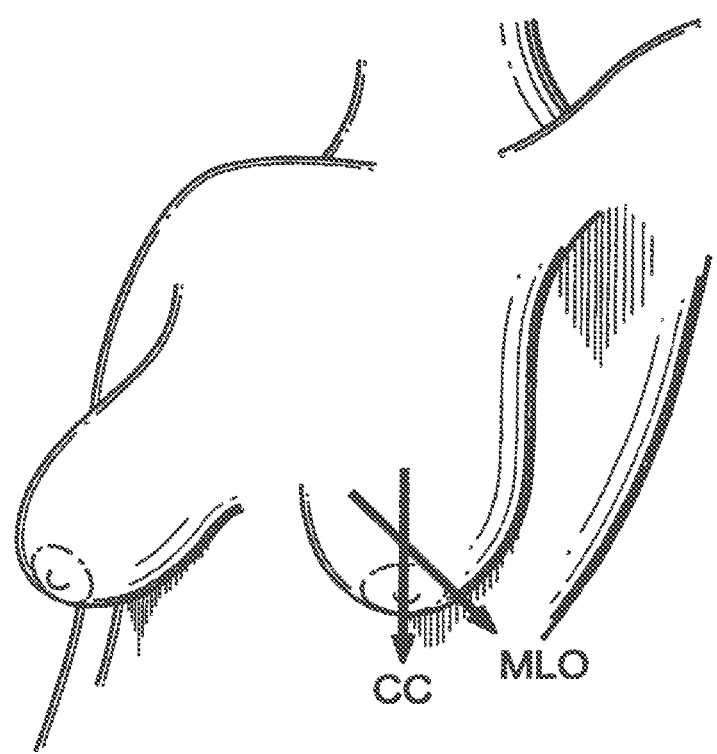
FIG. 5 illustrates two common x-ray protocols for breast imaging.

FIGS. 4a, 4b, and 4c illustrate an alternate arrangement for lateral adjustment of paddle 2. Here a paddle 2 of a selected size and possibly shape is removably secured to arm 6, and arm 6 is in turn slidably secured to frame 6 to slide laterally, along the direction of proximal edge 5a of receptor 6. The term "lateral" is used here to designate movement parallel to, or at least generally along, the proximal edge 5a, even when the imaging plane of receptor 5 is oriented for an MLO view or is vertical. For example, FIG. 4 can illustrate a position of paddle 2 for an MLO view of the left breast, FIG. 4b can illustrate a position for a CC view, and FIG. 4c can illustrate a position for an MLO view of the right breast.

It should be clear than many other arrangements are variations will be apparent to persons skilled in the technology based on the disclosure in this patent specification and that the above embodiments are only some of examples embodying inventions whose scope is defined by the appended claims.

The invention claimed is:

1. A mammography system comprising:
   A flat panel digital x-ray receptor having a proximal edge relative to a patient's breast to be imaged; and
   a compression paddle operably coupled such that the compression paddle moves generally along a length of the proximal edge of the receptor, wherein the compression paddle is configured to be secured in one or more positions along the length of the proximal edge of the receptor, at least one of the one or more positions of the compression paddle is off-center relative to the x-ray receptor.

2. The system of claim 1, wherein the compression paddle is configured to slide between the one or more positions.

3. The system of claim 1, wherein the compression paddle is secured in the one or more positions with an adjustable lock.

4. The system of claim 1, wherein the compression paddle is secured in the one or more positions with a detent.

5. The system of claim 4, wherein the compression paddle includes a channel to facilitate movement of the compression paddle relative to the x-ray receptor.

6. The system of claim 1, wherein the at least one of the one or more positions that is off-center relative to the x-ray receptor is for an MLO view of the patient's breast.

7. The system of claim 1 further comprising a scatter-reducing grid removably positioned between the compression paddle and the x-ray receptor.

8. The system of claim 1, wherein the scatter-reducing grid is in a first position for a first imaging mode and in a second position for a second imaging mode.

9. The system of claim 8, wherein the scatter-reducing grid is not positioned between the compression paddle and the x-ray receptor for the second imaging mode.

10. The system of claim 9 further comprising a motor coupled with the scatter-reducing grid for moving the grid between the first position and the second position.

11. The system of claim 1 further comprising an exposure control responsive to information regarding at least one of the one or more positions of the compression paddle.

12. A method of imaging a patient's breast with a mammography system comprising:
    providing a flat panel digital x-ray receptor having a proximal edge relative to a patient's breast to be imaged;
    securely positioning a compression paddle along a length of the proximal edge of the x-ray receptor, the compression paddle operably coupled such that the compression paddle moves generally along the length of the proximal edge of the receptor, wherein the compression paddle is configured to be secured in one or more positions along the length of the proximal edge of the receptor, at least one of the one or more positions of the compression paddle is off-center relative to the x-ray receptor;
    compressing the patient's breast between the x-ray receptor and the compression paddle; and
    imaging the patient's breast with x-rays from an x-ray source.

13. The method of claim 12, wherein securely positioning the compression paddle includes sliding the compression paddle between the one or more positions.

14. The method of claim 13, wherein the compression paddle is secured in the one or more positions with an adjustable lock.

15. The method of claim 13, wherein the compression paddle is secured in the one or more positions with a detent.

16. The method of claim 12 further removably positioning a scatter-reducing grid between the compression paddle and the x-ray receptor.

17. The method of claim 16, wherein the scatter-reducing grid is in a first position for a first imaging mode and in a second position for a second imaging mode.

18. The method of claim 17, wherein the scatter-reducing grid is not positioned between the compression paddle and the x-ray receptor for the second imaging mode.

19. The method of claim 17, wherein a motor coupled with the scatter-reducing grid moves the grid between the first position and the second position.

\* \* \* \* \*